United States Patent
Fujisaki (10) Patent No.: US 9,723,977 B2
(45) Date of Patent: Aug. 8, 2017

(54) INSERTION METHOD

(71) Applicant: OLYMPUS CORPORATION, Tokyo (JP)

(72) Inventor: Ken Fujisaki, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 170 days.

(21) Appl. No.: 14/632,693

(22) Filed: Feb. 26, 2015

(65) Prior Publication Data
US 2016/0249795 A1  Sep. 1, 2016

(51) Int. Cl.
*A61B 1/00* (2006.01)
*A61B 1/233* (2006.01)
*A61B 1/04* (2006.01)
*A61B 8/12* (2006.01)
*A61B 17/00* (2006.01)

(52) U.S. Cl.
CPC ............. *A61B 1/233* (2013.01); *A61B 8/12* (2013.01); *A61B 2017/00349* (2013.01)

(58) Field of Classification Search
CPC ............ A61B 1/233; A61B 1/04; A61B 1/018
See application file for complete search history.

(56) References Cited

U.S. PATENT DOCUMENTS

| 7,901,348 B2 * | 3/2011 | Soper | A61B 1/0008 600/117 |
| 8,206,349 B2 | 6/2012 | Slenker et al. | |
| 2009/0171301 A1 * | 7/2009 | Becker | A61M 3/0295 604/264 |
| 2010/0030031 A1 * | 2/2010 | Goldfarb | A61B 1/00066 600/163 |

OTHER PUBLICATIONS

Kumar et al., Accessory Maxillary Ostia: Topography and Clinical Application, J. Anal. Soc. India 50(1) (2001).*
Yoon et al., Fontanelle and Uncinate Process in the Lateral Wall of the Human Nasal Cavity, The Laryngoscope, Feb. 2001.*

* cited by examiner

*Primary Examiner* — Timothy J Neal
(74) *Attorney, Agent, or Firm* — Oliff PLC (57) ABSTRACT

An insertion method includes: specifying a part of a mucous membrane which lies between a nasal cavity and a maxillary sinus and which is located in a space surrounded by an inferior nasal concha, a lacrimal bone, an ethmoid bone, and a palatine bone, as an opening formation position where an opening connected to the maxillary sinus is formed; forming the opening at the opening formation position; and inserting a medical device into the maxillary sinus through the formed opening.

2 Claims, 11 Drawing Sheets

FIG.15

INSERTION METHOD

BACKGROUND OF THE INVENTION

1. Field of the Invention

The present invention relates to an insertion method for inserting a medical device for observing or treating the inside of a paranasal sinus, for example, the inside of a maxillary sinus.

2. Description of the Related Art

Conventionally, there is known a technique for inserting a medical device for treatment into a paranasal sinus and performing observation and treatment. As a related art for inserting a medical device into an opening in a nasal cavity connected to a paranasal sinus, for example, an opening connected to the paranasal sinus is formed in the nasal cavity, a medical device for observation or treatment is inserted through the artificially formed opening, and then the inside of the paranasal sinus is observed and/or a treatment is applied to a region to be treated.

SUMMARY OF THE INVENTION

An insertion method according to one aspect of the invention includes: specifying a part of a mucous membrane which lies between a nasal cavity and a maxillary sinus and which is located in a space surrounded by an inferior nasal concha, a lacrimal bone, an ethmoid bone, and a palatine bone, as an opening formation position where an opening connected to the maxillary sinus is formed; forming the opening at the opening formation position; and inserting a medical device into the maxillary sinus through the formed opening.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENT

Hereinafter, modes for carrying out the present invention (hereinafter referred to as an "embodiment") will be described in detail with reference to the drawings. The present invention is not limited by the embodiment described below. In the description below, each drawing only schematically illustrates shapes, sizes, and positional relationships at a level where content of the present invention can be understood. Therefore, the present invention is not limited by only the shapes, the sizes, and the positional relationships illustrated in each drawing.

Embodiment

Figure 1:
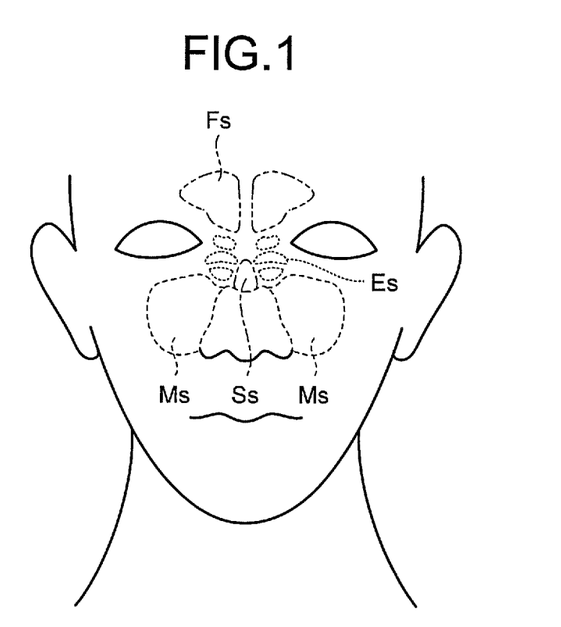
FIG. 1 is a schematic diagram illustrating a paranasal sinus.

FIG. 1 is a schematic diagram illustrating a paranasal sinus adjacent to a nasal cavity. As illustrated in FIG. 1, the paranasal sinus includes a frontal sinus Fs, an ethmoid sinus Es, a maxillary sinus Ms, and a sphenoid sinus Ss.

Figure 2:
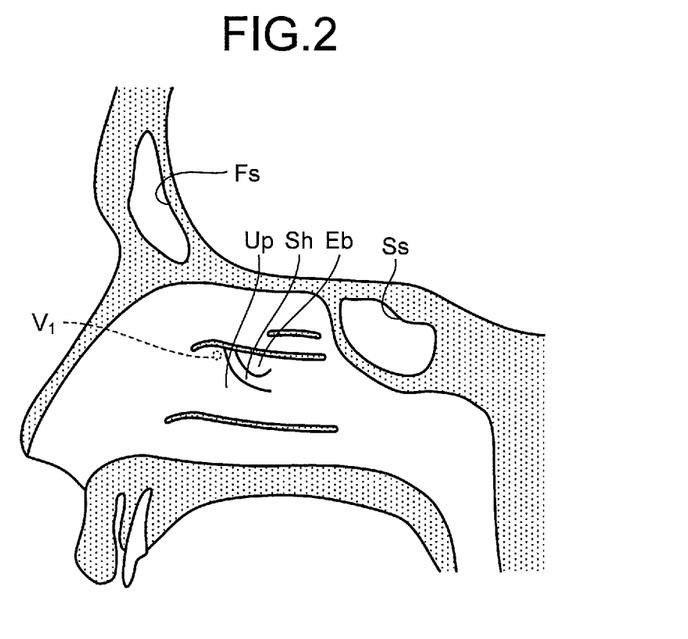
FIG. 2 is a schematic diagram illustrating an opening which is in a nasal cavity and which connects to a maxillary sinus.

FIG. 2 is a schematic diagram illustrating an opening which is in the nasal cavity and which connects to the maxillary sinus. The nasal cavity and the maxillary sinus communicate with each other through an opening. For example, in the nasal cavity, the aforementioned opening, which is an opening $V_1$ communicating with the maxillary sinus Ms illustrated in FIG. 1, is formed. However, as the opening $V_1$ is located on the back side of an uncinate process Up, it may be difficult to bring a medical device, such as an endoscope or a treatment tool, close to the opening $V_1$ and insert the medical device into the opening $V_1$. Hereinafter, in the present embodiment, an insertion method will be described, with which the medical device can be easily and less-invasively inserted into the maxillary sinus to observe and treat the inside of the maxillary sinus.

Subsequently, an observation process of the maxillary sinus including the insertion method according to the present embodiment will be described. FIGS. 3 to 9 are schematic diagrams illustrating the observation process of the maxillary sinus including the insertion method according to the embodiment. The present embodiment will be described assuming that a flexible endoscope (a flexible endoscope 120 described later) used as the medical device is inserted into the maxillary sinus Ms and the inside of the maxillary sinus Ms is observed.

Figure 3:
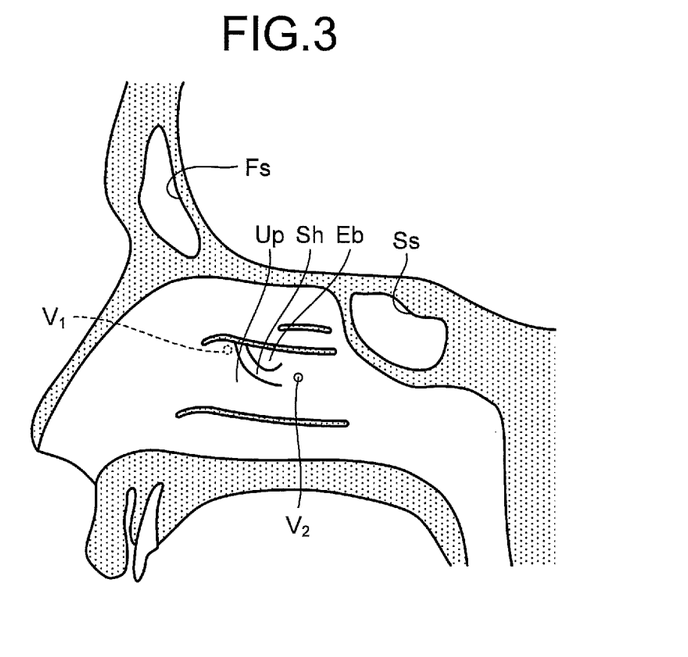
FIG. 3 is a schematic diagram illustrating an observation process of the maxillary sinus including an insertion method according to an embodiment of the present invention.
Figure 4:
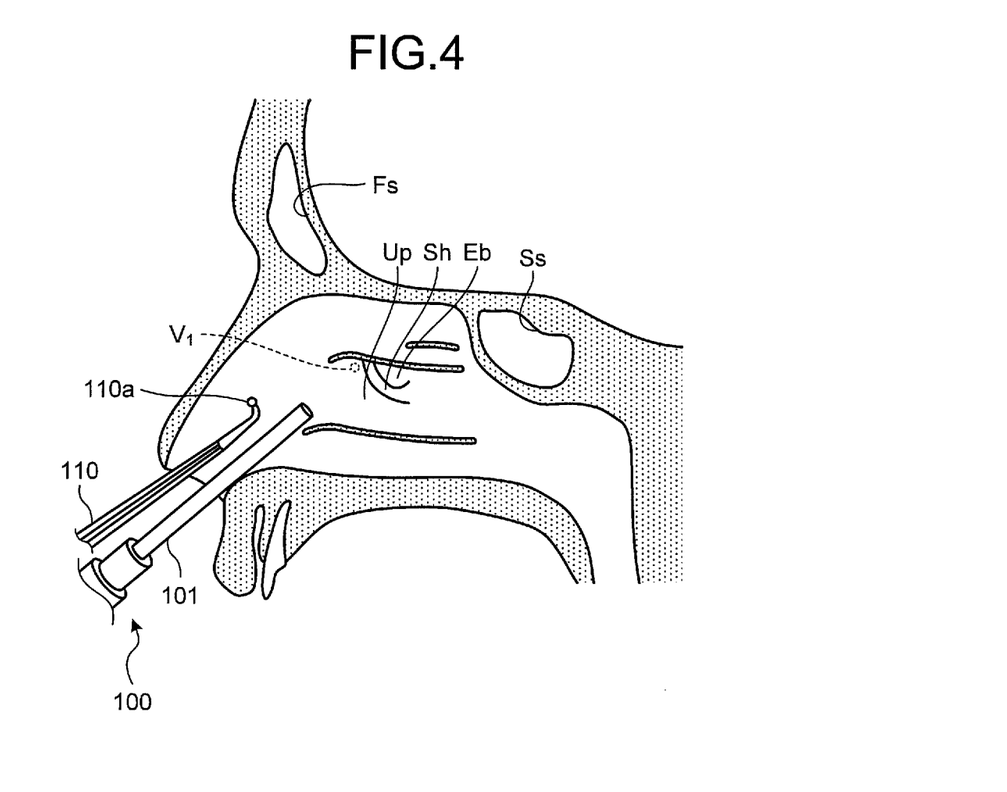
FIG. 4 is a schematic diagram illustrating the observation process of the maxillary sinus including the insertion method according to the embodiment of the present invention.
Figure 5:
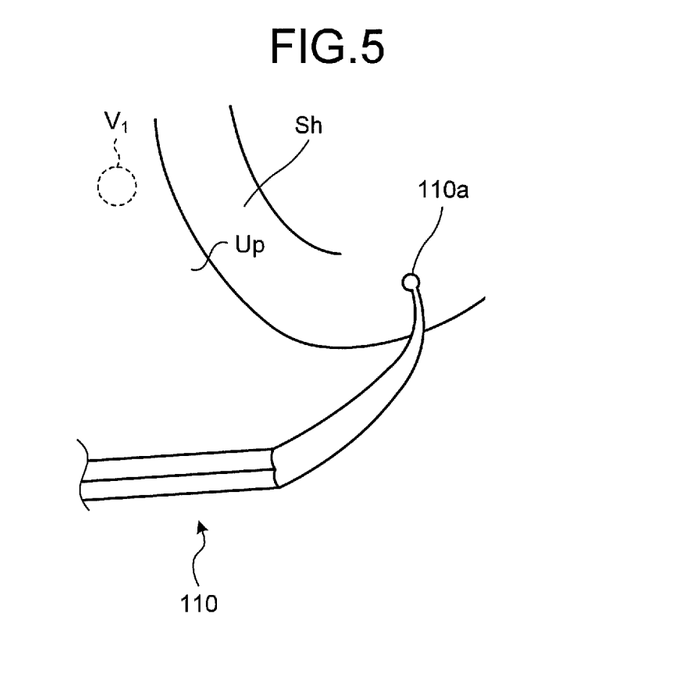
FIG. 5 is a schematic diagram illustrating the observation process of the maxillary sinus including the insertion method according to the embodiment of the present invention.

As illustrated in FIG. 3, in the insertion method according to the present embodiment, an opening $V_2$ different from the opening $V_1$ is formed at a position corresponding to a rear portion of a nasal fontanel in a mucous membrane which is a part of the maxillary sinus Ms in the nasal cavity, and the flexible endoscope 120 is inserted into the maxillary sinus Ms through the formed opening $V_2$.

An operator inserts an insertion unit 101 of a rigid endoscope 100 into the nasal cavity through a nostril of a subject. The operator inserts the insertion unit 101 into a middle nasal meatus and disposes a distal end of the insertion unit 101 at a position where a semilunar hiatus Sh is included in a visual field area of the rigid endoscope 100 while observing an intranasal image obtained by image-capturing by the rigid endoscope 100 (see FIG. 4).

Subsequently, the operator inserts a probe 110 in a state in which the insertion unit 101 is disposed in the nasal cavity. For example, the probe 110 has a shape tapering and curving toward the distal end and has a spherical object 110a at the distal end. The operator probes an opening formation position to insert the flexible endoscope (flexible endoscope 120) by causing the spherical object 110a to come into contact with a mucous membrane (see FIG. 5).

The probe 110 may be inserted into the nasal cavity at the same time as the rigid endoscope 100 or may be inserted after the nasal fontanel is confirmed by the rigid endoscope 100. When the probe 110 is inserted into the nasal cavity at the same time as the rigid endoscope 100, the rigid endoscope 100 may be inserted while maintaining the positional relationship between the rigid endoscope 100 and the probe 110 in a state in which the distal end (spherical object 110a) of the probe 110 is included in the visual field area of the rigid endoscope 100, or the rigid endoscope 100 may be inserted while maintaining the positional relationship between the rigid endoscope 100 and the probe 110 in a state in which the distal end (spherical object 110a) of the probe 110 is excluded from the visual field area of the rigid endoscope 100.

Figure 6:
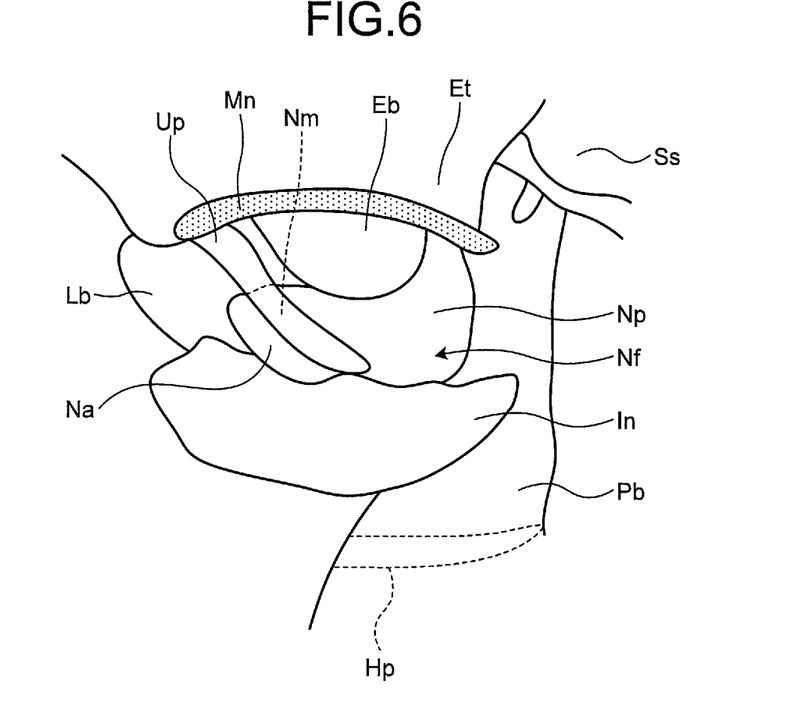
FIG. 6 is a schematic diagram illustrating the observation process of the maxillary sinus including the insertion method according to the embodiment of the present invention.

In the present embodiment, a mucous membrane which lies between the nasal cavity and the maxillary sinus Ms (a mucous membrane that forms a part of the maxillary sinus Ms in the nasal cavity) and which is a part of a mucous membrane located in a space (herein, referred to as a "nasal fontanel Nf") surrounded by an inferior nasal concha In, a lacrimal bone Lb, an ethmoid bone Et, and a palatine bone Pb as illustrated in FIG. 6 is defined as an opening formation position.

In FIG. 6, a middle nasal choncha Mn (sectional drawing), an ethmoidal bulla Eb, and a horizontal plate Hp are illustrated as a reference for regions in the nasal cavity. As the nasal fontanel Nf has no bone, it is not necessary break a bone when the opening $V_2$ is formed. Therefore, it is low invasive. In other words, it is preferable to form an opening in the nasal fontanel Nf.

Here, the nasal fontanel Nf is divided into the following three regions (first to third portions): a first portion Nm located on the back side of the uncinate process Up (a portion including the first opening $V_1$ connected to the maxillary sinus Ms); a second portion Na (Anterior Nasal Fontanelle (ANF)) located on the lacrimal bone Lb side of the uncinate process Up; and a third portion Np (Posterior Nasal Fontanelle (PNF)) located on the palatine bone Pb side of the uncinate process Up.

The operator specifies the opening formation position by a difference of repulsive force from a mucous membrane when causing the spherical object 110a of the probe 110 to come into contact with the mucous membrane, a difference of reflection of light in an intranasal image, and the like. While the opening can be formed in the aforementioned three regions (the first portion Nm, the second portion Na, and the third portion Np), it is preferable to specify the opening formation position in the third portion Np which is located on the back side of the uncinate process Up or is located at a position that can be reached without passing through the back side because it is easy to form the opening and it is easy for the medical device to access the opening.

Further, in the nasal fontanel Nf, the mucous membrane does not contain major arteries and neural paths and, therefore, major arteries and nerves are not damaged even when an opening is formed in the nasal fontanel Nf.

Figure 7:
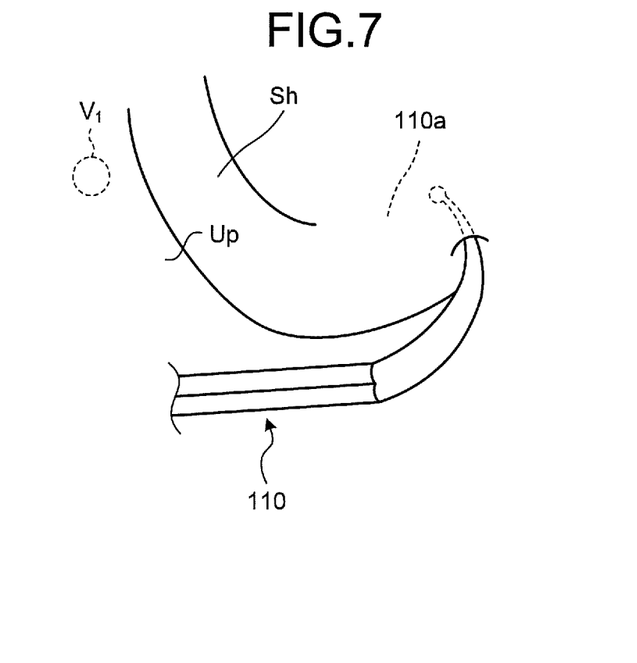
FIG. 7 is a schematic diagram illustrating the observation process of the maxillary sinus including the insertion method according to the embodiment of the present invention.

The operator specifies the opening formation position and, thereafter, forms the opening $V_2$ by pressing the spherical object 110a of the probe 110 against the specified opening formation position and piercing the mucous membrane (see FIG. 7).

Figure 8:
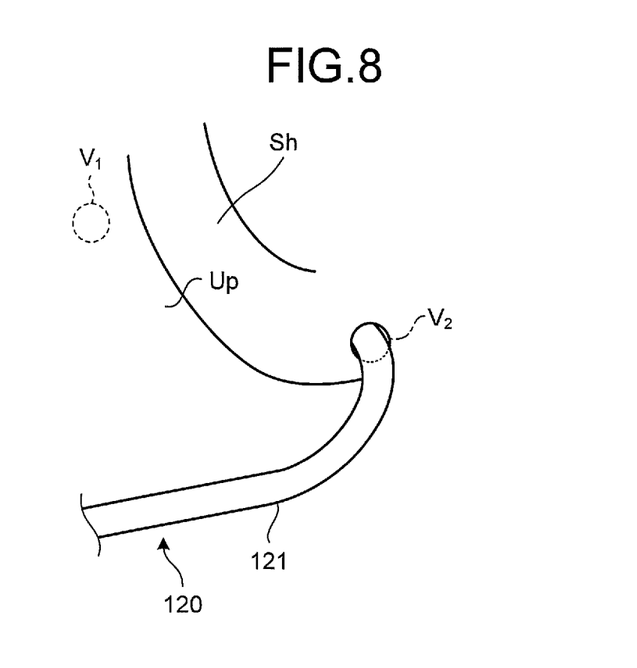
FIG. 8 is a schematic diagram illustrating the observation process of the maxillary sinus including the insertion method according to the embodiment of the present invention.

After the opening $V_2$ is formed, an insertion unit 121 of the flexible endoscope 120 is inserted into the maxillary sinus Ms through the opening $V_2$ (see FIG. 8). An image inside the paranasal sinus obtained by the flexible endoscope 120 may be displayed on the same display screen as that of the intranasal image obtained by the rigid endoscope 100 or may be displayed on each display screen of different monitors.

Figure 9:
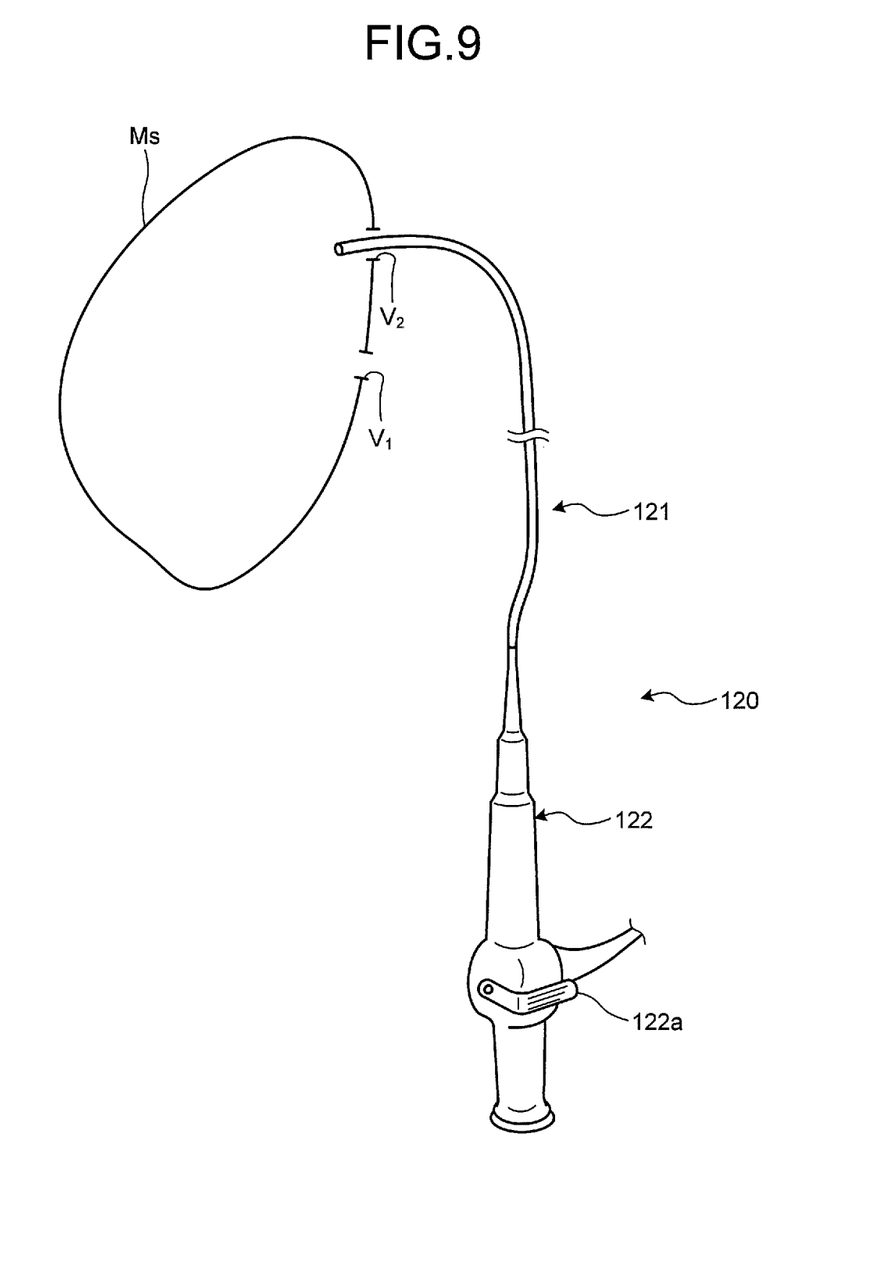
FIG. 9 is a schematic diagram illustrating the observation process of the maxillary sinus including the insertion method according to the embodiment of the present invention.

By the process described above, it is possible to form a state in which the distal end of the insertion unit 121 of the flexible endoscope 120 is inserted into the maxillary sinus Ms through the opening $V_2$ (see FIGS. 8 and 9).

As illustrated in FIG. 9, the flexible endoscope 120 includes the aforementioned insertion unit 121 and an operating unit 122, which is connected to a proximal end of the insertion unit 121 and operates the insertion unit 121. For example, the operator holds the proximal end or the central portion of the insertion unit 121 and the operating unit 122, inserts the insertion unit 121 into the maxillary sinus Ms, changes a curved shape of the distal end of the insertion unit 121 by operating a lever 122a and the like provided to the operating unit 122, and observes the inside of the maxillary sinus Ms while changing the visual field area.

Note that, besides the probe 110, a mucosal elevator, a knife, a small curette, a needle, a monopolar type or bipolar type electrical scalpel using a high-frequency current, an ultrasonic scalpel using an ultrasonic wave, a laser scalpel using a laser, and the like may be used to form the opening $V_2$ described above. The electrical scalpel and the laser scalpel are preferable in that these scalpels have a clotting hemostatic function.

Figure 10:
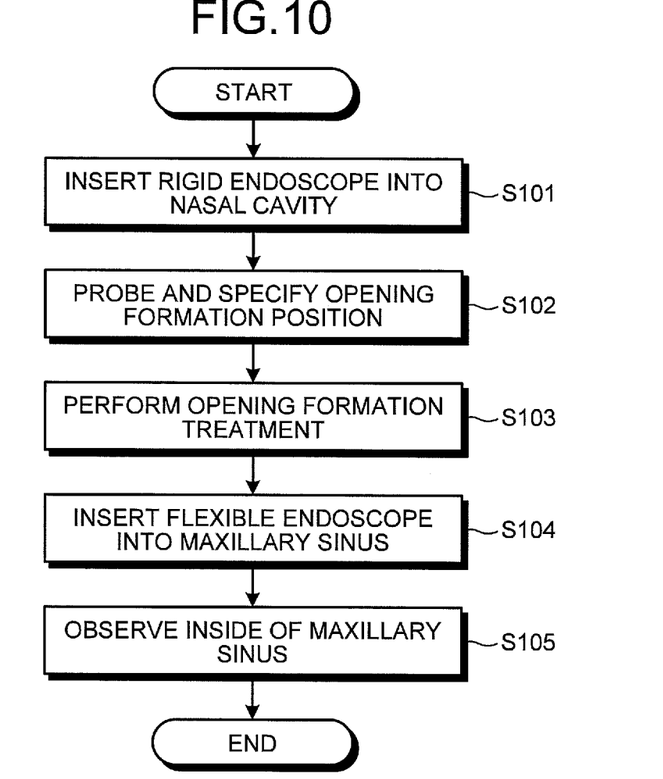
FIG. 10 is a flowchart illustrating the observation process of the maxillary sinus including the insertion method according to the embodiment of the present invention.

Here, a procedure of the aforementioned maxillary sinus treatment method will be described with reference to FIG. 10. FIG. 10 is a flowchart illustrating the observation process of the maxillary sinus including the insertion method according to the embodiment of the present invention. First, the operator inserts the rigid endoscope 100 into the nasal cavity (step S101). In this step, the operator disposes the rigid endoscope 100 at a position where the semilunar hiatus Sh is included in the visual field area.

Subsequently, the operator probes and specifies the opening formation position by using the probe 110 while observing the intranasal image obtained by the rigid endoscope 100 (step S102). In step S102, for example, the operator causes the spherical object 110a to come into contact with a mucous membrane and specifies the position where the opening $V_2$ is to be formed in, for example, the third portion Np of the nasal fontanel Nf described above. The operator probes the nasal fontanel Nf described above and specifies the opening formation position in the nasal fontanel Nf by, for example, detecting the presence or absence of a bone using a repulsive force from the mucous membrane.

The operator performs formation treatment of the opening $V_2$ after specifying the formation position of the opening $V_2$ (step S103). The operator forms the opening $V_2$ by, for example, pressing the spherical object 110a of the probe 110 against the mucous membrane and penetrating the mucous membrane.

The operator inserts the flexible endoscope 120 into the maxillary sinus Ms through the opening $V_2$ after forming the opening $V_2$ (step S104). In steps S101 and S102, the operator performs the insertion operation while capturing images with the rigid endoscope 100 and observing the captured images on a monitor or the like.

Thereafter, the operator performs observation of the inside of the maxillary sinus Ms by using images inside the paranasal sinus obtained by the flexible endoscope 120 (step S105).

Note that, if the opening $V_2$ is detected while the operator is probing the opening formation position in step S102, the operator proceeds to step S104. There is a case in which the opening $V_2$ has already been present because an opening formation treatment has been performed in the past or the opening $V_2$ originally existed.

According to the present embodiment described above, the formation position of the opening $V_2$ connected to the maxillary sinus Ms is specified in the nasal fontanel Nf by the probe 110 while the inside of the nasal cavity is observed by using the intranasal images obtained by the rigid endoscope 100, the opening $V_2$ is formed, and thereafter, the flexible endoscope 120 is inserted into the maxillary sinus Ms through the formed opening $V_2$. Accordingly, the flexible endoscope 120 can be easily and less invasively inserted into the maxillary sinus Ms. Conventionally, the flexible endoscope 120 is inserted into the maxillary sinus Ms through the opening $V_1$. However, as the opening $V_1$ is located on the back side of the uncinate process Up as seen from the nasal cavity (middle nasal meatus), the access in the opening may be difficult and/or there is a possibility that a bone located around the opening is broken depending on the type of the inserted medical device.

Further, according to the embodiment, the opening $V_2$ is formed at an arbitrary position of the nasal fontanel Nf in the nasal cavity, so that the opening can be formed at a position convenient for the operator. Therefore, the medical device can be more easily inserted than in a case where the medical device is inserted into the maxillary sinus through the opening that has already been formed.

In the embodiment described above, the opening formation position is specified by using the probe 110 while the intranasal images obtained by the rigid endoscope 100 are being observed. However, besides the intranasal images obtained by the rigid endoscope 100, the intranasal images obtained by the flexible endoscope 120 may be observed, ultrasonic images obtained by an ultrasonic endoscope may be observed, or the probe 110 may be inserted while visually observing the inside of the nasal cavity by expanding an opening of the nasal cavity using a nasoscope. Further, by displaying a nasal cavity model on the display screen and displaying the distal end position of the probe 110 in the nasal cavity, the probe 110 may be inserted while observing a display screen on which the distal end position of the probe 110 in the nasal cavity is mapped. Further, after the probe 110 is inserted into the nasal cavity, the opening formation position may be gropingly detected by feel through the spherical object 110a instead of the images and the visual observation.

First Modified Example of the Embodiment

Figure 11:
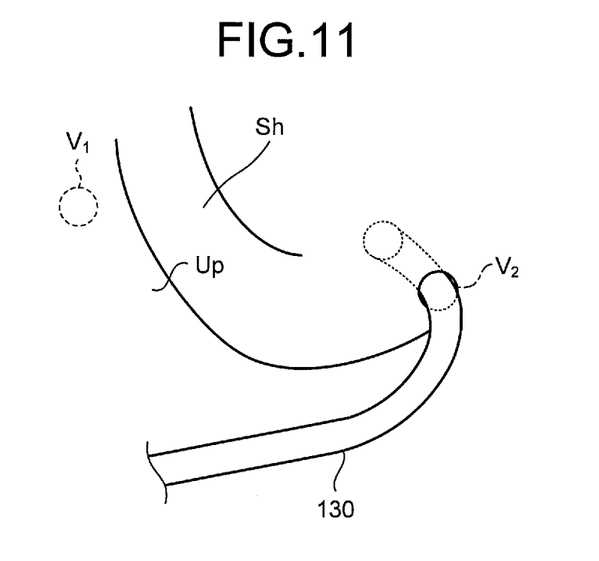
FIG. 11 is a schematic diagram illustrating an insertion method according to a first modified example of the embodiment of the present invention.

Next, a first modified example of the present embodiment will be described with reference to FIG. 11. FIG. 11 is a schematic diagram illustrating an insertion method according to the first modified example of the embodiment of the present invention. In the embodiment described above, it is described that the flexible endoscope 120 (the insertion unit 121) is inserted into the maxillary sinus Ms through the opening $V_2$. However, in the first modified example, a sheath 130 instead of the flexible endoscope 120 is inserted into the maxillary sinus Ms through the opening $V_2$.

The sheath 130 has a flexible cylindrical shape. When the sheath 130 is inserted into the maxillary sinus Ms, one end is located in the maxillary sinus Ms and the other end is connected to a pump not illustrated in FIG. 11. In the first modified example, a treatment, such as suctioning pus and the like accumulated in the maxillary sinus from the one end of the sheath 130 by suction of the pump and discharging a medical agent from the one end of the sheath 130 by transfer from the pump, can be applied in the maxillary sinus Ms.

Second Modified Example of the Embodiment

Figure 12:
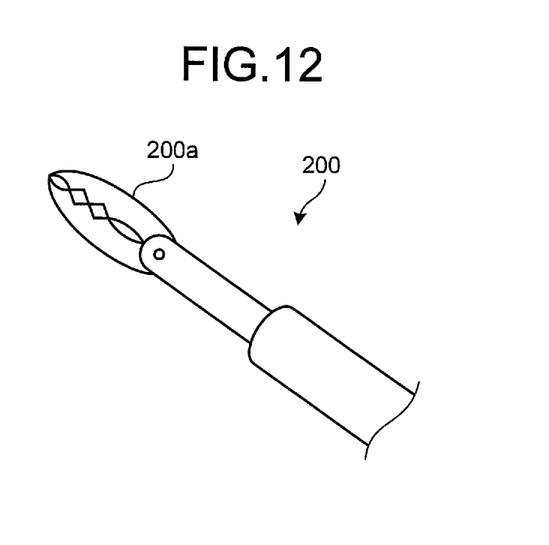
FIG. 12 is a schematic diagram illustrating an insertion method according to a second modified example of the embodiment of the present invention and is a schematic diagram illustrating an example of a treatment tool to be inserted into the maxillary sinus.

Next, a second modified example of the present embodiment will be described with reference to FIG. 12. FIG. 12 is a schematic diagram illustrating an insertion method according to the second modified example of the embodiment of the present invention, and is a schematic diagram illustrating an example of a treatment tool to be inserted into the maxillary sinus. In the embodiment described above, it is described that the flexible endoscope 120 (the insertion unit 121) is inserted into the maxillary sinus Ms through the opening $V_2$. However, in the second modified example, the treatment tool is inserted into the maxillary sinus Ms and a treatment in the paranasal sinus is performed.

A treatment tool 200 according to the second modified example has an elongated shape having flexibility and includes biopsy forceps 200a at its distal end. For example, it is possible to sample some tissues in the maxillary sinus Ms by inserting the treatment tool 200 into the maxillary sinus Ms through the opening $V_2$ and grasping a region to be treated using the biopsy forceps 200a. The opening and closing operation of the biopsy forceps 200a is operated by an operating unit (not illustrated in FIG. 12) provided at the proximal end of the treatment tool 200 and a wire (not illustrated in FIG. 12) that connects the operating unit and the biopsy forceps 200a.

Third Modified Example of the Embodiment

Figure 13:
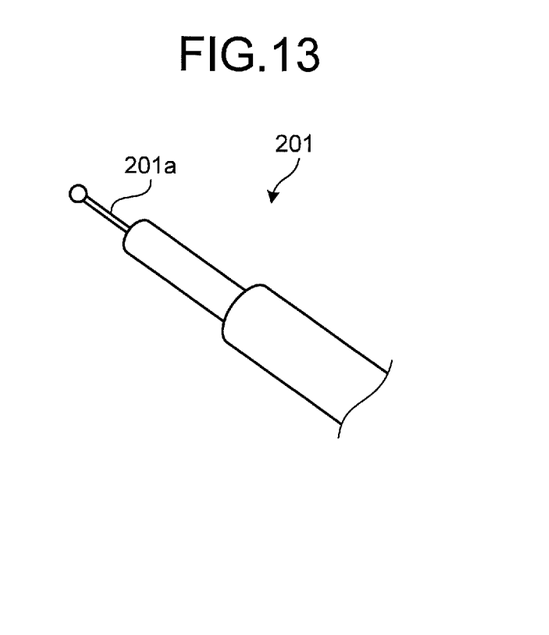
FIG. 13 is a schematic diagram illustrating an insertion method according to a third modified example of the embodiment of the present invention and is a schematic diagram illustrating an example of a treatment tool to be inserted into the maxillary sinus.

Next, a third modified example of the present embodiment will be described with reference to FIG. 13. FIG. 13 is a schematic diagram illustrating an insertion method according to the third modified example of the embodiment of the present invention, and is a schematic diagram illustrating an example of a treatment tool to be inserted into the maxillary sinus. In the embodiment described above, it is described that the flexible endoscope 120 (the insertion unit 121) is inserted into the maxillary sinus Ms through the opening $V_2$. However, in the third modified example, the treatment tool is inserted into the maxillary sinus Ms and a treatment in the paranasal sinus is performed.

A treatment tool 201 according to the third modified example has an elongated shape having flexibility and includes a high-frequency knife 201a at its distal end. For example, it is possible to incise or exfoliate a part of a lesional tissue and/or an exogenous material in the maxillary sinus Ms by inserting the treatment tool 201 into the maxillary sinus Ms through the opening $V_2$ and causing the high-frequency knife 201a to come into contact with a region to be treated. An on state and an off state of electric current for the high-frequency knife 201a are switched by, for example, operating an operating unit (not illustrated in FIG. 13) connected to the proximal end of the treatment tool 201. Besides the high-frequency knife, a treatment tool that can emits a laser for cauterizing a region to be treated, a treatment tool that can emits a sterilizing laser, and the like may be used.

Fourth Modified Example of the Embodiment

Figure 14:
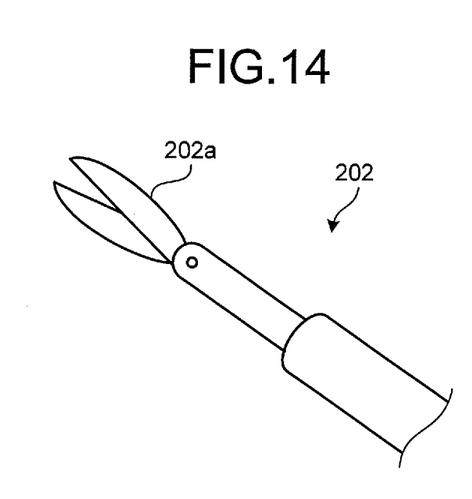
FIG. 14 is a schematic diagram illustrating an insertion method according to a fourth modified example of the embodiment of the present invention and is a schematic diagram illustrating an example of a treatment tool to be inserted into the maxillary sinus.

Next, a fourth modified example of the present embodiment will be described with reference to FIG. 14. FIG. 14 is a schematic diagram illustrating an insertion method according to the fourth modified example of the embodiment of the present invention, and is a schematic diagram illustrating an example of a treatment tool to be inserted into the maxillary sinus. In the embodiment described above, it is described that the flexible endoscope 120 (the insertion unit 121) is inserted into the maxillary sinus Ms through the opening $V_2$. However, in the fourth modified example, the treatment tool is inserted into the maxillary sinus Ms and a treatment in the paranasal sinus is performed.

A treatment tool 202 according to the fourth modified example has an elongated shape having flexibility and includes scissors 202a at its distal end. For example, it is possible to extirpate some tissues in the maxillary sinus Ms by inserting the treatment tool 202 into the maxillary sinus Ms through the opening $V_2$ and holding a region to be treated using the scissors 202a. The opening and closing operation of the scissors 202a is operated by, for example, an operating unit (not illustrated in FIG. 14) provided at the proximal end of the treatment tool 202 and a wire (not illustrated in FIG. 14) that connects the operating unit and the scissors at the distal end.

Fifth Modified Example of the Embodiment

Figure 15:
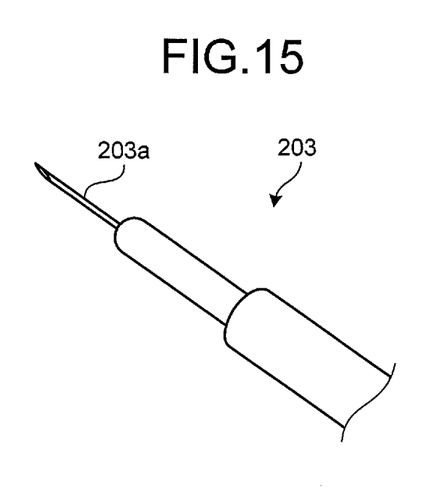
FIG. 15 is a schematic diagram illustrating an insertion method according to a fifth modified example of the embodiment of the present invention and is a schematic diagram illustrating an example of a treatment tool to be inserted into the maxillary sinus.

Next, a fifth modified example of the present embodiment will be described with reference to FIG. 15. FIG. 15 is a schematic diagram illustrating an insertion method according to the fifth modified example of the embodiment of the present invention, and is a schematic diagram illustrating an example of a treatment tool to be inserted into the maxillary sinus. In the embodiment described above, it is described that the flexible endoscope 120 (the insertion unit 121) is inserted into the maxillary sinus Ms through the opening $V_2$. However, in the fifth modified example, the treatment tool is inserted into the maxillary sinus Ms and a treatment in the paranasal sinus is performed.

A treatment tool 203 according to the fifth modified example has an elongated shape having flexibility and includes an injection needle 203a at its distal end. For example, it is possible to sticking the injection needle 203a into tissues in the maxillary sinus Ms and injecting medicine into the tissues by inserting the treatment tool 203 into the maxillary sinus Ms through the opening $V_2$ and sticking the injection needle 203a into a region to be treated. The injection needle 203a is provided with, for example, an operating unit (a syringe and a piston) (not illustrated in FIG. 15) provided at the proximal end of the treatment tool 203 and a tube (not illustrated in FIG. 15) that connects the operating unit and the injection needle 203a. Delivery of medicine through the tube or suction of liquid from the maxillary sinus Ms through the tube are performed by an operation of the operating unit.

The treatment tools 200 to 203 according to the second to the fifth modified examples described above may be inserted into the maxillary sinus Ms after inserting them into the sheath 130 according to the first modified example.

In the embodiment and the modified examples described above, it is described that the medical device such as the flexible endoscope 120, the sheath 130, the treatment tool 200, and the like are directly inserted into the opening $V_2$. However, the medical device may be caused to access a region close to the opening $V_2$ by using an insertion assisting tool. The insertion assisting tool may be a tool including a guide sheath into which the aforementioned medical device can be inserted and a tool including a guide member that guides the medical device in the proceeding direction and a movement unit which holds the medical device and is able to move along the guide member.

The present invention is not limited to the embodiment and the modified examples described above, and may include various embodiments without departing from the scope of technical ideas described in the appended claims.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An insertion method comprising:
   probing, using a probe, a part of a mucous membrane to determine an opening formation position, the part of the mucous membrane being located between a nasal cavity and a maxillary sinus, and being located in a space surrounded by an inferior nasal concha, a lacrimal bone, an ethmoid bone, and a palatine bone;
   forming an opening connected to the maxillary sinus at the determined opening formation position, by using the probe; and
   inserting a medical device into the maxillary sinus through the formed opening.
2. The insertion method according to claim 1, wherein the opening formation position is determined by a repulsive force from the mucous membrane.

* * * * *